United States Patent [19]

Elliott et al.

[11] 4,294,823

[45] Oct. 13, 1981

[54] ASTRINGENT OR DEGREASING LOTION

[75] Inventors: Thomas J. Elliott, London; David Ford, Isleworth, both of England

[73] Assignee: Beecham Group Limited, England

[21] Appl. No.: 107,275

[22] Filed: Dec. 26, 1979

Related U.S. Application Data

[63] Continuation of Ser. No. 965,790, Dec. 4, 1978, abandoned.

[30] Foreign Application Priority Data

Nov. 26, 1977 [GB] United Kingdom ............... 49304/77

[51] Int. Cl.$^3$ ...................... A61K 7/00; A61K 7/035; A61K 7/48; A61K 31/74
[52] U.S. Cl. ......................................... 424/78; 424/81; 424/83; 424/358; 424/365
[58] Field of Search ...................... 424/69, 78, 79, 81, 424/358, 365

[56] References Cited

FOREIGN PATENT DOCUMENTS

| | | | |
|---|---|---|---|
| 2113453 | 12/1971 | Fed. Rep. of Germany | 424/69 |
| 774029 | 5/1957 | United Kingdom | 424/69 |
| 1093108 | 11/1967 | United Kingdom | 424/69 |
| 1141994 | 2/1969 | United Kingdom | 424/69 |
| 1202796 | 8/1970 | United Kingdom | 424/69 |

*Primary Examiner*—Anna P. Fagelson
*Attorney, Agent, or Firm*—Jacobs & Jacobs

[57] ABSTRACT

A skin care product such as a cleansing lotion or pre- or aftershave lotion comprising ethanol, water, spherical polymer or copolymer microspheres, e.g. of polyethylene, polystyrene or polymethylmethacrylate, and a suspending agent for the microspheres. The ethanol:water weight ratio is in the range 1:19 to 19:1 and the microspheres, which may be sized from 5 to 7 microns, amount to 3 to 10% by weight of the product. The microspheres have a smoothing and matting effect on the skin, improving the observed degreasing effect of the product.

1 Claim, No Drawings

ASTRINGENT OR DEGREASING LOTION

CROSS-REFERENCE

This is a continuation of Ser. No. 965,790 filed Dec. 4, 1978, abandoned.

This invention relates to a skin-care product comprising an aqueous alcoholic solution with tiny polymer particles suspended therein. The product is of value as, for example, an aftershave or preshave preparation or as a cleansing lotion.

Aqueous alcoholic solutions are common toiletries preparations. Usually they are lightly perfumed and used as cleansing lotions for degreasing the skin or as mild astringents in pre- or aftershave applications. However, their effects on the skin are short lived, lasting only for a few minutes before fresh sebum production and the relaxation of the skin cells restores the normal appearance of the skin.

It has now been found that if small amounts of tiny polymer particles are suspended in such aqueous alcoholic solutions, a long lasting skin smoothing and matting effect can be obtained.

Accordingly, the present invention provides a skin care product comprising ethanol, water, spherical or substantially spherical synthetic polymer or copolymer particles and a suspending agent for the polymer or copolymer particles, the weight ratio of ethanol:water being from 1:19 to 19:1 and the polymer or copolymer particles being present in an amount from 3 to 10% by weight.

The polymer or copolymer particles should preferably not swell to any great extent in the ethanol/water solution. Within this limitation cross-linked polystyrene or polymethylmethacrylate microspheres would be suitable. However, the preferred polymer is polyethylene.

Usually the product will contain from 3 to 5% by weight of the polymer of copolymer particles.

Preferably the polymer or copolymer particles shall have an average particle size of from 5 to 7 microns.

The ratio of ethanol:water present in the product will depend on the drying time required on the skin as well as on the astringency and degreasing power required of the product. Higher ethanol ratios result in quick drying and higher degreasing power, more appropriate to a product intended as a cleansing lotion. Lower ethanol ratios result in slower drying and milder degreasing, more appropriate to an aftershave product.

It is necessary to increase the viscosity of the ethanol/water solution to prevent the sedimentation of the polymer or copolymer particles. For this reason a suspending agent is included in the product of the invention. Any cosmetically acceptable suspending agent capable of increasing the viscosity of the solution or of otherwise preventing the sedimentation of the polymer or copolymer particles would be suitable. A common agent useful in the present invention is a carboxyvinyl polymer sold under the trade name "Carbopol 940". In use this agent is preferably neutralised with a cosmetically acceptable base such as di-isopropranolamine.

It will be appreciated that the polmyer and copolymer particles are very small and light, and that consequently very little of the suspending agent will be required to prevent sedimentation. On the other hand, if a thicker more viscous solution is desired for any reason more of the suspending agent could certainly be added.

Usually the product of the invention will be perfumed.

For some applications, particularly as an aftershave, the product of the invention may contain a cosmetically acceptable emollient. Such emollients should be soluble in the ethanol/water mixture. An example of a suitable emollient is the polyol fatty acid ester sold under the trade name "Cetiol H.E."

The effect of the product of the invention is to produce an improvement in the smoothness of the skin due to the action of the polymer or copolymer microspheres as dry lubricants, and an additional benefit is achieved in reducing the apparent oiliness of greasy skins by the matting effect of the microspheres.

The following is an example of the composition of a product in accordance with the invention, suitable for use as an aftershave:

| | |
|---|---|
| Ethyl alcohol | 40.00% w/w |
| Distilled Water | 45.73% w/w |
| Carbopol 940 | 0.17% w/w |
| Di-isopropanol | 0.10% w/w |
| *Polymist B6 | 10.00% w/w |
| Cetiol H.E. | 2.00% w/w |
| Perfume | 2.00% w/w |

*"Polymist" is a trade mark of Allied Chemicals, Station House, Stamford New Road, Altrincham, Cheshire, England.

Polymist B6 is a high density (0.96 gm/cc by ASTM D-1505) polyethylene in the form of microspheres having an average particle size of $6\mu$ with less than 2% of the particles larger than $10\mu$.

We claim:

1. A cosmetic ethanol:water based astringent or degreasing lotion which provides a long lasting smoothing and matting effect comprising in suspension in said lotion base from 3 to 10% by weight of spherical or substantially spherical particles of polystyrene, polymethylmethacrylate or polyethylene, said particles having an average particle side of 5 to 7 microns, together with a skin emoillent and a cosmetically acceptable suspending agent, said ethanol: water being present relative to one another in a ratio of from 1:19 to 19:1.

* * * * *